US006461869B1

(12) United States Patent
Schwarzenberger et al.

(10) Patent No.: US 6,461,869 B1
(45) Date of Patent: Oct. 8, 2002

(54) PURGING LEUKEMIA CELLS FROM HEMATOPOIETIC STEM CELLS

(75) Inventors: Paul Schwarzenberger; Jay Kolls, both of New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/357,752

(22) Filed: Jul. 20, 1999

(51) Int. Cl.$^7$ .................. C12N 15/86; C12N 15/00; C12N 5/00; C12P 21/06; C07H 21/04
(52) U.S. Cl. ................ 435/456; 435/69.1; 435/320.1; 435/325; 424/93.1; 424/93.2; 424/93.21; 536/24.1
(58) Field of Search ............................... 424/93.1, 93.2, 424/93.21; 435/69.1, 320.1, 325, 456; 514/44; 536/24.1

(56) References Cited

U.S. PATENT DOCUMENTS

| | | | |
|---|---|---|---|
| 5,521,291 A | * | 5/1996 | Curiel et al. ............. 530/391.7 |
| 5,877,010 A | * | 3/1999 | Loeb et al. .............. 435/320.1 |
| 5,885,808 A | * | 3/1999 | Spooner et al. ........... 435/172.3 |
| 6,284,504 B1 | * | 9/2001 | Wei et al. .................. 435/183 |
| 6,312,946 B1 | * | 11/2001 | Yeh et al. ................ 435/320.1 |

OTHER PUBLICATIONS

Verma et al. Nature. 389: 239–242, Sep. 1997.*
Goodman & Gilman's Pharmacological Basis of Therapeutics, 9th Ed. Chap. 5, Eck et al. McGraw–Hill. pp. 77–101, 1995.*
Schwarzenberger et al, Blood, vol. 87, pp. 472–478, 1996.*
Schwarzenberger et al. J of Virology, vol. 71, pp. 8563–8571, Nov. 1997.*
Seth et al. J Cancer Res, vol. 56, pp. 1346–1351, 1996.*
Schwarzenberger, slides presented at the Sep. 24–25, 1998 meeting of the Leukemia Society, 1996.*
Chen, L. et al., "Selective transgene expression for detection and elimination of contaminating carcinoma cells in hematopoietic stem cell sources," *J. Clin. Invest.*, vol. 98, pp. 2539–2548 (1996).
Schwarzenberger, P. et al., "Targeted gene transfer to human hematopoietic progenitor cell lines through the c–kit receptor," *Blood*, vol. 87, pp. 472–478 (1996).

Schwarzenberger, P., "Development of a gene therapy based bone marrow purging system for leukemia patients," Abstract, 1998 Translational Research Progress Review Meeting, Leukemia Society of America (Sep. 24–25, 1998).
Schwarzenberger, P., "Development of a gene therapy based bone marrow purging system for leukemia patients," *Leukemia Society of America Annual Report 1998, Appendix: Abstracts of Grants in Force*, p. 82 (1999).
Schwarzenberger, P. et al., "Receptor–targeted recombinant adenovirus conglomerates: a novel molecular conjugate vector with improved expression characteristics," *J. Virol.*, vol. 71, pp. 8563–8571 (1997).
Schwarzenberger, "Development of a gene therapy based bone marrow purging system for leukemia," slides presented at the Sep. 24–25, 1998 meeting of the Leukemia Society.
Seth, P. et al., "Adenovirus–mediated gene transfer to human breast tumor cells: An approach for cancer gene therapy and bone marrow purging," *J. Cancer Res.*, vol. 56, pp. 1346–1351 (1996).
Seth, P. et al., "A recombinant adenovirus expressing wild type p53 induces apoptosis in drug–resistant human breast cancer cells: A gene therapy approach for drug–resistant cancers," *Cancer Gene Ther.*, vol. 4, pp. 383–390 (1997).
Wilson, J., "When bad gene transfer is good," *J. Clin. Invest.*, vol. 98, p. 2435 (1996).

* cited by examiner

*Primary Examiner*—Deborah J. Reynolds
*Assistant Examiner*—Eleanor Sorbello
(74) *Attorney, Agent, or Firm*—John H. Runneis

(57) ABSTRACT

A gene therapy system is disclosed that selectively kills leukemia cells in bone marrow, while leaving stem cells unaffected. All cells in a mixture of stem cells and leukemia cells are transfected with a high efficiency gene transfer vector. The vector carries a eukaryotic expression construct encoding a toxin gene. This toxin gene is expressed only in leukemia cells, not in stem cells. Differential expression of the toxin gene in leukemia cells and stem cells may be achieved by placing the coding sequence under the control of an appropriate promoter, such as the RSV promoter or the SV40 promoter. High gene expression has been demonstrated in a panel of transformed leukemia cell lines, but no gene expression in transformed, CD34-selected, primary human stem cells. The treatment will be useful not only for leukemia patients, but also for other cancer patients undergoing autologous bone marrow transplants (e.g., breast or lymphoma cancers).

5 Claims, No Drawings

PURGING LEUKEMIA CELLS FROM HEMATOPOIETIC STEM CELLS

This invention pertains to a method and composition for purging leukemia cells from hematopoietic stem cells.

For many leukemia patients, the only hope for cure or long term survival is a bone marrow transplant from a donor. The cells for these "allogeneic" transplants are generally obtained from a sibling or from an unrelated, HLA-matched donor. However only a small fraction of potential patients receive such transplants due to constraints such as advanced age or the lack of a matching donor. Therefore, "autologous" marrow transplants are also used at times, the re-infusion of cells from the patient's own bone marrow following chemotherapy or radiation therapy that otherwise destroys the patient's marrow. Bone marrow is taken from a patient prior to high dose chemotherapy or radiation therapy, and is later reinfused to "rescue" the patient following the otherwise lethal therapy. However, there is currently no effective procedure to completely remove contaminating leukemia cells from bone marrow or other stem cell preparations. On the one hand, an autologous transplant does not carry the risk of short- or long-term graft-versus-host-disease, since the patient receives back his or her own bone marrow. However, a major drawback of existing autologous techniques is the lack of an effective way to remove all contaminating cancer cells from the bone marrow ex vivo. Relapses frequently result from such contaminating cancer cells. In principle, autologous transplants should be superior to allogeneic transplants if a method could be found to completely purge the transplanted cells of contaminating leukemia cells, because the risk of host-versus-graft disease would be eliminated.

Progress has been made in reducing relapse rates in autologous transplants. Various purging procedures have been used to selectively remove leukemia cells from bone marrow, such as ex vivo chemotherapy with 4-hydrocyclophosphamide, or fractionation of cells by size. The combination of these two techniques, ex vivo chemotherapy with fractionation of cells by size, would probably be considered the current state-of-the art purging procedure by most researchers. However, this combination therapy often does not completely purge leukemic cells from the transplanted material.

So-called hematopoietic "stem cells" are critical in reconstituting a destroyed immune system and reconstituting red blood cell synthesis. Stem cells express the CD34 molecular marker on the cell surface. A different approach to purging bone marrow of leukemia cells is to select for cells expressing the CD34 molecule, for example by affinity chromatography using monoclonal anti-CD34 antibodies. This selection reduces the number of malignant cells, although it does not eliminate them entirely. A patient infused with the CD34 fraction of bone marrow cells will reconstitute hematopoiesis completely. CD34 selection of hematopoietic stem cells is currently being explored as an alternative purging system in autologous transplants.

Although a several log-fold reduction in leukemia cell number has been seen with these prior purging procedures, significant numbers of malignant cells are still present after purging. Currently there is no purging procedure that can completely eradicate leukemic cells from contaminated bone marrow. There is a continuing need for improved methods to efficiently purge bone marrow cells of leukemia cells.

P. Seth et al., "A recombinant adenovirus expressing wild type p53 induces apoptosis in drug-resistant human breast cancer cells: A gene therapy approach for drug-resistant cancers," *Cancer Gene Ther.*, vol. 4, pp. 383–390 (1997) discloses that a recombinant adenovirus expressing the wild type tumor suppressor gene p53 induced apoptosis in two drug-resistant human breast cancer cell lines, and that the recombinant virus selectively induced apoptosis in the breast cancer cells when the latter were mixed with CD34 cells. The differential targeting resulted from the fact that breast cancer cells express high levels of adenovirus receptors, while bone marrow cells are deficient in adenovirus receptors. See also P. Seth et al., "Adenovirus-mediated gene transfer to human breast tumor cells: An approach for cancer gene therapy and bone marrow purging," *J. Cancer Res.*, vol. 56, pp. 1346–1351 (1996).

Similarly, L. Chen et al., "Selective transgene expression for detection and elimination of contaminating carcinoma cells in hematopoietic stem cell sources," *J. Clin. Invest.*, vol. 98, pp. 2539–2548 (1996) discloses the use of replication-defective adenoviral vectors to selectively transduce breast cancer cells in the presence of bone marrow cells. Using an adenoviral vector to transduce the HSV-tk gene allowed the selective killing of breast cancer cells with ganciclovir with little effect on CFU-GM and BFU-E formulation or on long term culture initiating cells. See also J. Wilson, "When bad gene transfer is good," *J. Clin. Invest.*, vol. 98, p. 2435 (1996).

Unfortunately, adenovirus-based vectors are not well-suited for treating leukemias because adenovirus uptake by leukemia cells is poor.

We have discovered a gene therapy system that selectively kills leukemia cells in bone marrow, while leaving stem cells unaffected. All cells in a mixture of stem cells and leukemia cells are transfected with a high efficiency gene transfer vector. The vector carries a eukaryotic expression construct encoding a toxin gene. This toxin gene is expressed only in leukemia cells, not in stem cells. Differential expression of the toxin gene in leukemia cells and stem cells may be achieved by placing the coding sequence under the control of an appropriate promoter, such as the RSV promoter or the SV40 promoter. To the inventors' knowledge, there have been no prior reports of specific differential regulation of genes in leukemia cells and stem cells.

Using a molecular conjugate vector, we have demonstrated high gene expression in a panel of transformed leukemia cell lines, but no gene expression in transformed, CD34-selected, primary human stem cells. We have demonstrated high levels of gene expression in leukemia cells, and essentially no expression in stem cells. We have also demonstrated the selective killing of leukemia cells mixed with a population of CD34 bone marrow cells.

The novel treatment will be useful not only for leukemia patients, but also for other cancer patients undergoing autologous bone marrow transplants (e.g., breast or lymphoma cancer patients).

The coding sequence may either directly encode a toxin, or it may encode a conditionally toxic peptide such as HSV-tk. The HSV-tk gene product is conditionally lethal, as that product is an enzyme that converts ganciclovir into a toxin. (Other toxins that could be used in this invention are discussed below.)

In a clinical setting,, a construct in accordance with this invention is transferred with high efficiency into a suspension of a human patient's bone marrow cells, containing both the patient's stem cells and leukemia cells. Since expression of the toxin gene is restricted to leukemic cells, only those cells will be eliminated. Since the toxin gene is not expressed in hematopoietic stem cells, the stem cells survive the purging procedure. The novel purging system can be used in autologous bone marrow transplants either by itself, or in conjunction with other purging systems. The combination of this system with others (e.g. ex vivo chemotherapy, fractionation of cells by size, selection for the CD34 marker) should be able to eliminate leukemic cells from stem cells completely. The construct is preferably designed so that the trans-gene is present only transiently, and does not integrate into the genome of the stem cells. Experimental Results.

EXAMPLE 1

In a prototype proof of concept demonstration, we used a polylysine-based molecular conjugate gene transfer vector to selectively induce expression of a reporter molecule in leukemia cells but not in stem cells. The polylysine vector transforms both leukemia cells and hematopoietic stem cells with nearly 100% efficiency. The polylysine vector used to transform the gene of interest into leukemia cells was that of P. Schwarzenberger et al., "Targeted gene transfer to human hematopoietic progenitor cell lines through the c-kit receptor," *Blood,* vol. 87, pp. 472–478 (1996); and P. Schwarzenberger et al., "Receptor-targeted recombinant adenovirus conglomerates: a novel molecular conjugate vector with improved expression characteristics," *J. Virol.,* vol. 71, pp. 8563–8571 (1997). Other high efficiency vectors could also be used, such as an RGD-adenovirus, and other viruses modified to express polylysine on the viral surface. Significant reporter gene expression was seen in human leukemia cell lines using the molecular conjugate vector with the RSV and SV40 promoters, but essentially no expression was seen in CD34-selected human bone marrow cells with these promoters.

Leukemia cell lines or CD34-selected hematopoietic stem cells were transfected with the Ad-PL polylysine vector and luciferase reporter constructs under different promoters (CMV, RSV and SV40).

Transfection. Briefly, 100 μl of adenovirus—PL (AD-PL) was condensed with 2 μg of either reporter plasmid or toxin constructs for 30 min. at room temperature. Cell suspensions ($1 \times 10^6$ cell/ml) in serum-reduced medium (2% FCS) were incubated with these vectors in a 1.5 ml Eppendorf tube at 37° C. with rotation for 2 hours. Cells were then returned to regular growth conditions in a 25 ml flask. Cells were harvested at different times and analyzed for luciferase expression (Promega, Madison, Wis.) using a luminometer (Berthold, Bad Wildung, Germany and Analytical Chemiluminescence, San Diego, Calif.), with a measuring time of 20 seconds. Relative light units (RLU's) measured were corrected for the protein concentration of the cell lysate (Pierce, Rockford, Ill.) and are reported as RLU/mg of protein.

Chemical linkage of adenovirus (AD) and recombinant adenovirus (recAD) to polylysine (PL). The procedure was performed as described in P. Schwarzenberger et al., "Targeted gene transfer to human hematopoietic progenitor cell lines through the c-kit receptor," *Blood,* vol. 87, pp. 472–478 (1996); and P. Schwarzenberger et al., "Receptor-targeted recombinant adenovirus conglomerates: a novel molecular conjugate vector with improved expression characteristics," *J. Virol.,* vol. 71, pp. 8563–8571 (1997). Briefly, E1-deleted human type 5 AD (dl312) and E1-deleted human serotype 5 recombinant AD containing the luciferase gene under the control of a CMV promoter (recombination of pJM17 and pAC-CMV-luc) were used to infect 293 cells (gifts from Dr. Thomas Shenk, Princeton, N.J. and Dr. David Curiel, Birmingham, Ala.). Cells were harvested when a cytopathic effect was observed. Following four freeze-thaw cycles, the cell lysate was purified twice over a cesium chloride gradient by ultracentrifugation. Adenovirus was covalently linked to polylysine (Sigma, St. Louis, Mo.) with EDC (Pierce, Rockford, Ill.) to achieve a final concentration of $5 \times 10^{11}$ particles/ml (1 OD at 260 nm equals $10^{12}$ viral particles, or $1 \times 10^{10}$ plaque forming units (pfu) prior to linkage). Aliquots of AD, recAD, AD-PL, and recAD-PL were stored in viral preservation medium at −70° C. (0.01 M Tris, pH 8, 0.1 M NaCl, 0.1% BSA, 10% glycerol).

Multiplicity of infection (moi). Moi for AD dl312 and recAD were standardized by number of plaque forming units (pfu). Pfu was determined by performing plaque forming assays using 293 cells following the procedure outlined in J. Kolls et al., "Prolonged and effective blockade of tumor necrosis factor activity through adenovirus-mediated gene-transfer," *Proc. Natl. Acad. Sci. USA,* vol. 91, pp. 215–219 (1994).

Chemical linkage of Streptavdin (SA) to Polylysine (PL). Streptavidin (Sigma) was linked to PL (Sigma) as previously described in P. Schwarzenberger et al., "Targeted gene transfer to human hematopoietic progenitor cell lines through the c-kit receptor," *Blood,* vol. 87, pp. 472–478 (1996); and P. Schwarzenberger et al., "Receptor-targeted recombinant adenovirus conglomerates: a novel molecular conjugate vector with improved expression characteristics," *J. Virol.,* vol. 71, pp. 8563–8571 (1997). The SA and PL content were determined by OD at 280 nm and 223 nm respectively. PL was modified with streptavidin at a molar ratio of 1:6.25, for a final concentration of 300 μg/ml PL and 40 μg/ml streptavidin.

Construction of Plasmid DNA. The plasmid pLUC4 was prepared by cloning the luciferase gene under the control of the cytomegalovirus promoter into the plasmid pSTCXSSC (obtained from Dr. David Curiel, Gene Therapy Program, University of Alabama, Birmingham). The HSV-tk gene was obtained from Dr. Scott Freeman, Tulane University. Using the BamH1 and Kpn1 restriction sites, the HSV-tk gene was cloned into the multiple cloning site of pREP8 (RSV), pCEP4 (CMV), and pSV40 (SV40) (inVitrogen, Carlsbad, Calif.). Endotoxins from plasmid DNA preparations were removed by Quiagen columns prior to transfection.

Results. We observed that the CMV-driven constructs resulted in the highest levels of gene expression in all cell lines; i.e., CMV did not provide selectivity. High levels of luciferase activity were seen in leukemia cells with RSV and SV40 promoters, but there was essentially no luciferase expression in CD34 primary stem cells; i.e., both RSV and SV40 provided a high degree of selectivity. See Table I, giving levels of luciferase activity in relative light units for the different systems, expressed as mean ± standard error.

TABLE I

Levels of Luciferase Activity in Different Transformed Systems

|  | CMV | RSV | SV40 |
|---|---|---|---|
| MBO2 | $(5.24 \pm 0.82) \times 10^6$ | $(2.19 \pm 0.14) \times 10^6$ | $(9.9 \pm 1.2) \times 10^3$ |
| MO7-E | $(9.8 \pm 1.2) \times 10^5$ | $(2.38 \pm 0.15) \times 10^5$ | $(3.50 \pm 0.25) \times 10^3$ |
| K562 | $(6.1 \pm 1.2) \times 10^6$ | $(9.0 \pm 1.3) \times 10^5$ | $(7.7 \pm 0.1) \times 10^4$ |
| TF1 | $(5.49 \pm 0.88) \times 10^5$ | $(8.9 \pm 0.8) \times 10^4$ | $(9.8 \pm 2.9) \times 10^2$ |
| U937 | $(7.7 \pm 0.8) \times 10^5$ | $(5.98 \pm 0.59) \times 10^4$ | $(4.9 \pm 0.25) \times 10^3$ |
| THP1 | $(3.4 \pm 0.55) \times 10^5$ | $(4.1 \pm 0.8) \times 10^4$ | $(2.2 \pm 0.3) \times 10^3$ |
| CD34 + BM | $(2.2 \pm 0.1) \times 10^4$ | $60 \pm 71$ | $31 \pm 0$ |
| CD34 + PB | $(1.9 \pm 0.1) \times 10^4$ | $42 \pm 39$ | $33 \pm 0$ |

Notes to Table I: MBO2 (myelo/megakaryocytic leukemia cell line), MO7e (myelo/megakaryocytic leukemia cell line), K562 (erythroleukemia), TF1 (myelocytic leukemia cell line), U937 (monocytic leukemia), THP1 (monocytic leukemia), CD34 BM (human stem cells obtained from donor marrow), CD34 PB (human stem cells obtained from peripheral blood after G-CSF mobilization). CMV (Cytomegalovirus promoter-luciferase), RSV (respiratory syncytial virus promoter-luciferase), SV40 (Simian Virus 40 promoter-luciferase). The CD34 cell lines were obtained from consenting volunteers through the Louisiana State University Medical Center bone marrow transplantation program (Dr. R. W. Veith, New Orleans.) All other cell lines were obtained from the National Cancer Institute in Bethesda, Md., and are also available through the American Type Culture Collection.

EXAMPLE 2

We have also demonstrated the selective killing of leukemia cells in a mixture of leukemia cells and stem cells. RSV-MCV-HSV-tk+ganciclovir selectively eliminated leukemia cells admixed with human stem cells in an experiment performed in triplicate. ("MCV" denotes molecular conjugate vector.) $1 \times 10^6$ human CD34-selected bone marrow cells obtained from a normal donor were mixed with $1 \times 10^5$ K562-115 erythroleukemia cells. The mixture of cells was transfected with an amount of RSV-MCV-HSV-tk sufficient to kill $1 \times 10^6$ K562-115 cells, as had been determined for this vector lot in prior experiments (data not shown). (This amount was determined separately for each lot, to allow for lot-to-lot variations.) Ganciclovir (50 $\mu$M) was added to the medium 24 hours post-transfection. Luciferase assays were performed on days 0, 1, 5, and 10 to determine presence of K562-115 cells. See Table II. Luciferase activity decreased rapidly following transfection. The decrease in luciferase activity was accompanied by a 20% decrease in colony-forming units (GM-GEMM and HPP) (corrected for the number of leukemia colony-forming units). (Abbreviations used: GM, granulocyte macrophage; GEMM, granulocyte erythrocyte megakaryocyte monocyte; HPP, high proliferative potential (in reference to a colony forming unit).) No luciferase activity at all was detected in the ganciclovir-treated specimens after day 5, whereas in control samples (no ganciclovir) luciferase activity gradually recovered to 100% (data not shown). (The control samples exhibited a decrease because the one-time purging procedure itself has some toxicity; i.e., exposure with the vector alone will kill some cells.) Evaluation of colony formation of the purged marrow cells demonstrated no significant decrease compared to control after day 5 (GM, GEMM and HPP).

TABLE II

RSV-MCV-HSV-tk + ganciclovir in CD34+ stem cells contaminated with 10% K562-115 erythroleukemia cells

|  | RLU | CFU | CFU-HPP |
|---|---|---|---|
| Day 0 | 100 | 100 | 100 |
| Day 1 | 43 | 79 | 72 |
| Day 5 | 0 | 64 | 54 |
| Day 10 | 0 | 52 | 41 |

Notes to Table II: RLU (relative light units, a measure of luciferase activity), CFU (colony forming units, measured in semisolid agar, with a colony defined as over 50 cells), HPP (High proliferative Potential colonies, defined as over 200 cells). Subtypes are GM and GEMM.

These results demonstrated that a construct comprising the toxin gene HSV-tk under the control of the RSV promoter selectively killed leukemia cells contaminating a stem cell suspension, while preserving the replating ability of the stem cells.

An additional replication of the above experiment produced similar results (data not shown).

Promoters suitable for use in this invention are those causing differential expression between hematopoietic stem cells and leukemia cells. Differential expression may be enhanced by the use of viral-derived promoters, such as those from SV40 or respiratory syncytial virus.

Ex vivo and in vivo treatments in animal leukemia models will be conducted before trials involving human patients. For example, we plan to conduct treatments in the A20 mouse leukemia model. The A20 line is a very aggressive mouse leukemia line. Mouse bone marrow will be contaminated with A20 cells, and then infused into mice either with or without purging in accordance with the present invention, and results will be observed.

We also plan to use the NOD-SCID mouse model (non-obese-diabetic, severe-combined-immunodeficiency) to test the effect of purging on primary human stem cells that are transplanted into NOD-SCID mice. NOD-SCID mice are a recognized in vivo model to test human cells.

Following the successful conclusion of the animal experiments, ex vivo and in vivo clinical trials to treat human leukemia patients will be conducted in accordance with applicable laws and regulations.

Toxins Suitable for Use in the Present Invention

In addition to the HSV-tk gene, genes encoding any of a number of other toxins may also be used in the present invention. As used in the specification and claims, a "toxin" may either be a molecule that is directly toxic to a cell expressing the molecule, or a molecule that is conditionally toxic, e.g., one that depends on the presence of a co-factor (e.g., ganciclovir) for toxicity. Preferably, a toxin should have the following characteristics:

(1) The toxin should be capable of being readily produced under the regulatory control of a promoter, i.e., a peptide or protein. For example, a suitable toxin may be one of the many toxic peptides known in the art.

(2) The toxin should kill only the cell in which it is expressed, and not neighboring cells.

There are numerous toxins from plants, animals, and bacteria satisfying these criteria. For example, there are many bacterial toxins that use an A/B subunit motif, in which the A subunit is toxic once it enters a cell but has no ability to cross cell membranes unassisted, and in which the B subunit (or multi-subunit complex) binds to cells but has no toxicity on its own. The A subunit, even when injected systemically, is non-toxic. See, e.g., Balfanz, L., Rautenberg, P., and U. Ullmann. 1996. Molecular mechanisms of action of bacterial exotoxins. Zbl. Bakt. 284: 170–206.; Middlebrook, J. L. and R. B. Dorland. 1984. Bacterial toxins: cellular mechanisms of action. Microbiological Reviews. 48: 199–221. Nucleic acids coding for the A or active subunit could be used in this invention because the A subunit will already be inside the cell when it is produced, so it will not be necessary to include sequences coding for the B or cell-binding component. The A subunit will kill the cell in which it is expressed, but will not damage other cells when released by cell lysis because the A subunit could not gain access to the interior of other cells. Examples include the A subunit of cholera toxin, which destroys ion balance, and the A subunit of diphtheria toxin, which terminates protein synthesis. Other toxins comprise a single peptide chain having separate domains, where one domain functions to enable entry into the cell and a second domain is toxic. Such a multidomain peptide toxin could be truncated, using genetic engineering to produce a construct that only codes for the toxin domain. Use of a truncated toxin that is only expressed within target cells, and that cannot enter other cells, avoids the problem of general toxicity with respect to nontarget cells. One example of a truncated toxin that has been used in other systems to kill artificially targeted cells is the truncated form of exotoxin A from *Pseudomonas aeruginosa.* Pastan, I., and FitzGerald, D. 1991. Recombinant toxins for cancer treatment. Science 254: 1173–1177. The commonly used ricin toxin from plants also uses this same type of A/B subunit motif. Lee, H. P. et al., "Immunotoxin Therapy for Cancer," *JAMA,* vol. 269, pp. 78–81 (1993).

With such "catalytic" toxins, very few toxin molecules— even as few as a single molecule— would need to be expressed to kill a target cell. Catalytic toxins such as diphtheria toxin A polypeptide have been successfully used (in another context) to selectively kill cell lineages in transgenic mice. See R. Palmiter et al., "Cell lineage ablation in transgenic mice by cell-specific expression of a toxin gene," *Cell,* vol. 50, pp. 435–443 (1987).

Other classes of "non-catalytic" peptide toxins may also be useful, such as the class of peptides called "lytic peptides," or "antimicrobial amphipathic peptides." These peptides are relatively small, generally containing 20 to 50 amino acids (or even fewer), and are capable of forming an amphipathic alpha helix in a hydrophobic environment, wherein at least part of one face is predominantly hydrophobic and at least part of the other face is predominately hydrophilic and is positively charged at physiological pH. Such structures can be predicted by applying the amino acid sequence to the Edmundson helical wheel (Schiffer, M., and A. B. Edmundson. 1967. Use of the helical wheel to represent the structures of proteins and to identify segments with helical potential. Biophys. J. 7:121–135.). In addition to their small size, such peptides are widely distributed in nature and vary significantly in toxicity. They can also be designed to possess different levels of lytic activity. Typically, when applied to cells in culture, a few micrograms per ml are required to kill the cells. The level of toxicity of lytic peptides is determined by the amino acid composition and sequence. Different peptides can have widely differing levels of toxicity. In addition, relatively few molecules should be needed to kill a cell if the cell produces the molecules internally. A further discussion of lytic peptides suitable for use in this invention appears below.

Cloning of lytic peptide genes.

Due to the role played by lytic peptides in nature, especially to protect against bacterial infections, the production of lytic peptides by various cloning technologies has been widely investigated and published. A consistent finding of workers who have attempted to express lytic peptides by cloning is that the lytic peptides kill the cells expressing the cloned lytic peptide gene, thereby seriously reducing product yields. In nature most lytic peptides are produced with signal sequences directing the product to be stored in membrane-bound vesicles, to be secreted on mucosal surfaces. Investigators have overcome this "killing problem" either by using mechanized peptide synthesizers, or by generating fusion proteins that are non-lytic until the lytic domain has been cleaved from the carrier domain.

In this context, the killing of the cell producing the cloned lytic peptide has been viewed as an unwanted consequence, resulting in failure of the experiment. By contrast, in the present invention the killing of cells that produce the cloned lytic peptide does not represent a failed experiment, but rather is the desired consequence in eliminating leukemia cells.

Successful cloning and expression of various lytic peptides in cultured cells, in plants, and in animals is well documented See, e.g., Gudmundsson, G. H., Lidholm, D. A., Asling, B., Gan, R., and H. G. Boman. 1991. The cecropin locus: cloning and expression of a gene cluster encoding three antibacterial peptides in *Hyalophora cecropia.* J. Biol. Chem. 266: 11510–11517.; Cooper and Enright, U.S. patent application Ser. No. 08/491,609, filed Jun. 7, 1995 and affidavits submitted therein; and U.S. Pat. No. 5,556,782. Recently, genes encoding lytic peptides, under the control of promoters inducible in response to bacterial endotoxins, have been successfully cloned into catfish and shown to be functional to produce the lytic peptide in response to endotoxin. Cooper and Enright, U.S. patent application Ser. No. 08/491,609, filed Jun. 7, 1995 and affidavits submitted therein. Genes encoding lytic peptides have also been successfully genetically engineered into plants. See Hightower, R., Baden, C., Penzes, E., and P. Dunsmuir. 1994. The expression of cecropin peptide in transgenic tobacco does not confer resistance to *Pseudomonas syringe pv tabaci.* Plant Cell Rep. 13: 295–299.; Allefs, S., Florack, D. Hoogendoorn, C., and W. J. Stiekeme. 1995. Erwinia soft rot resistance of potato cultivars transformed with a gene construct coding for antimicrobial peptide cecropin B is not altered. Am. Potato J. 72: 437–445; Florack, D., Allefs, S., Bollen, R., Bosch, D., Visser, B., and W. Stiekema. 1995. Expression of giant silkmoth cecropin B encoding genes in transgenic tobacco. *Transgenic Research* 4: 132–141.; Jaynes, J. M., Nagpala, P., Destefano-Beltran, L., Huang, J. H., Kim, J., Denny, T., and S. Cetiner. 1993. Expression of a cecropin B lytic peptide analog in transgenic tobacco confers enhanced resistance to bacterial wilt caused by

*Pseudomonas solanacearum.* Plant Sci. 89: 43–53.; and U.S. Pat. Nos. 5,597,946 and 5,597,945.

Lytic Peptides Useful in the Present Invention.

Many lytic peptides are known in the art and include, for example, those mentioned in the references cited in the following discussion.

Lytic peptides are small, basic peptides. Native lytic peptides appear to be major components of the antimicrobial defense systems of a number of animal species, including those of insects, amphibians, and mammals. They typically comprise 23–39 amino acids, although they can be smaller. For example, the protegrins from porcine leukocytes have 16–18 amino acids, and fragments down to 12 amino acids show activity against bacteria. See X-D Qu et al., "Protegrin Structure and Activity against *Neisseria gonorrhoea,*" *Infection and Immunity,* vol. 65, pp. 636–639 (1997). Some designed peptides show activity at even shorter lengths. See McLaughlin et al., cited below.

Lytic peptides have the potential for forming amphipathic alpha-helices. See Boman et al., "Humoral immunity in *Cecropia pupae,*" *Curr. Top. Microbiol. Immunol.* vol. 94/95, pp. 75–91 (1981); Boman et al., "Cell-free immunity in insects," *Ann. Rev. Microbiol.,* vol. 41, pp. 103–126 (1987); Zasloff, "Magainins, a class of antimicrobial peptides from Xenopus skin: isolation, characterization of two active forms, and partial DNA sequence of a precursor," *Proc. Natl. Acad. Sci. USA,* vol. 84, pp. 3628–3632 (1987); Ganz et al., "Defensins natural peptide antibiotics of human neutrophils," *J. Clin. Invest.,* vol. 76, pp. 1427–1435 (1985); and Lee et al., "Antibacterial peptides from pig intestine: isolation of a mammalian cecropin," *Proc. Natl. Acad. Sci. USA,* vol. 86, pp. 9159–9162 (1989).

Known amino acid sequences for lytic peptides may be modified to create new peptides that would also be expected to have lytic activity by substitutions of amino acid residues that preserve the amphipathic nature of the peptides (e.g., replacing a polar residue with another polar residue, or a non-polar residue with another non-polar residue, etc.); by substitutions that preserve the charge distribution (e.g., replacing an acidic residue with another acidic residue, or a basic residue with another basic residue, etc.); or by lengthening or shortening the amino acid sequence while preserving its amphipathic character or its charge distribution. Lytic peptides and their sequences are disclosed in Yamada et al., "Production of recombinant sarcotoxin IA in Bombyx mori cells," *Biochem. J.,* vol. 272, pp. 633–666 (1990); Taniai et al., "Isolation and nucleotide sequence of cecropin B cDNA clones from the silkworm, *Bombyx mori,*" *Biochimica Et Biophysica Acta,* vol. 1132, pp. 203–206 (1992); Boman et al., "Antibacterial and antimalarial properties of peptides that are cecropin-melittin hybrids," *Febs Letters,* vol. 259, pp. 103–106 (1989); Tessier et al., "Enhanced secretion from insect cells of a foreign protein fused to the honeybee melittin signal peptide," *Gene,* vol. 98, pp. 177–183 (1991); Blondelle et al., "Hemolytic and antimicrobial activities of the twenty-four individual omission analogs of melittin," *Biochemistry,* vol. 30, pp. 4671–4678 (1991); Andreu et al., "Shortened cecropin A-melittin hybrids. Significant size reduction retains potent antibiotic activity," *Febs Letters,* vol. 296, pp. 190–194 (1992); Macias et al., "Bactericidal activity of magainin 2: use of lipopolysaccharide mutants," *Can. J. Microbiol.,* vol. 36, pp. 582–584 (1990); Rana et al., "Interactions between magainin-2 and Salmonella typhimurium outer membranes: effect of Lipopolysaccharide structure," *Biochemistry,* vol. 30, pp. 5858–5866 (1991); Diamond et al., "Airway epithelial cells are the site of expression of a mammalian antimicrobial peptide gene," *Proc. Natl. Acad. Sci. USA,* vol. 90, pp. 4596 ff (1993); Selsted et al., "Purification, primary structures and antibacterial activities of β-defensins, a new family of antimicrobial peptides from bovine neutrophils," *J. Biol. Chem., vol.* 268, pp. 6641 ff (1993); Tang et al., "Characterization of the disulfide motif in BNBD-12, an antimicrobial β-defensin peptide from bovine neutrophils," *J. Biol. Chem.,* vol. 268, pp. 6649ff(1993); Lehrer et al., *Blood,* vol. 76, pp. 2169–2181 (1990); Ganz et al., *Sem. Resp. Infect. I.,* pp. 107–117 (1986); Kagan et al., *Proc. Natl. Acad. Sci. USA,* vol. 87, pp. 210–214 (1990); Wade et al., *Proc. Natl. Acad. Sci. USA,* vol. 87, pp. 4761–4765 (1990); Romeo et al., *J. Biol. Chem., vol.* 263, pp. 9573–9575 (1988Jaynes et al., "Therapeutic Antimicrobial Polypeptides, Their Use and Methods for Preparation," WO 89/00199 (1989); Jaynes, "Lytic Peptides, Use for Growth, Infection and Cancer," WO 90/12866 (1990); Berkowitz, "Prophylaxis and Treatment of Adverse Oral Conditions with Biologically Active Peptides," WO 93/01723 (1993).

Families of naturally-occurring lytic peptides include the cecropins, the Defensins, the sarcotoxins, the melittins, and the magainins. Boman and coworkers in Sweden performed the original work on the humoral defense system of *Hyalophora cecropia,* the giant silk moth, to protect itself from bacterial infection. See Hultmark et al., "Insect immunity. Purification of three inducible bactericidal proteins from hemolymph of immunized pupae of *Hyalophora cecropia,*" *Eur. J. Biochem.,* vol. 106, pp. 7–16 (1980); and Hultmark et al., "Insect immunity. Isolation and structure of cecropin D. and four minor antibacterial components from cecropia pupae," *Eur. J. Biochem.,* vol. 127, pp. 207–217 (1982).

Infection in *H. cecropia* induces the synthesis of specialized proteins capable of disrupting bacterial cell membranes, resulting in lysis and cell death. Among these specialized proteins are those known collectively as cecropins. The principal cecropins—cecropin A, cecropin B, and cecropin D—are small, highly homologous, basic peptides. In collaboration with Merrifield, Boman's group showed that the amino-terminal half of the various cecropins contains a sequence that will form an amphipathic alpha-helix. Andrequ et al., "N-terminal analogues of cecropin A: synthesis, antibacterial activity, and conformational properties," *Biochem.,* vol. 24, pp. 1683–1688 (1985). The carboxy-terminal half of the peptide comprises a hydrophobic tail. See also Boman et al., "Cell-free immunity in Cecropia," *Eur. J. Biochem.,* vol. 201, pp. 23–31 (1991).

A cecropin-like peptide has been isolated from porcine intestine. Lee et al., "Antibacterial peptides from pig intestine: isolation of a mammalian cecropin," *Proc. Natl. Acad. Sci. USA,* vol. 86, pp. 9159–9162 (1989).

Defensins, originally found in mammals, are small peptides containing six to eight cysteine residues. Ganz et al., "Defensins natural peptide antibiotics of human neutrophils," *J. Clin. Invest.,* vol. 76, pp. 1427–1435 (1985). Extracts from normal human neutrophils contain three defensin peptides: human neutrophil peptides HNP-1, HNP-2, and HNP-3. Defensin peptides have also been described in insects and higher plants. Dimarcq et al., "Insect immunity: expression of the two major inducible antibacterial peptides, defensin and diptericin, in *Phormia terranvae,*" *EMBO J.,* vol. 9, pp. 2507–2515 (1990); Fisher et al., *Proc. Natl. Acad. Sci. USA,* vol. 84, pp. 3628–3632 (1987).

Slightly larger peptides called sarcotoxins have been purified from the fleshfly *Sarcophaga peregrina.* Okada et al., "Primary structure of sarcotoxin I, an antibacterial protein induced in the hemolymph of *Sarcophaga peregrina* (flesh fly) larvae," *J. Biol. Chem.,* vol. 260, pp. 7174–7177

(1985). Although highly divergent from the cecropins and Defensins, the sarcotoxins presumably have a similar antibiotic function.

Other lytic peptides have been found in amphibians. Gibson and collaborators isolated two peptides from the African clawed frog, *Xenopus laevis,* peptides which they named PGS and $Gly^{10}Lys^{22}$PGS. Gibson et al., "Novel peptide fragments originating from $PGL_a$ and the caervlein and xenopsin precursors from *Xenopus laevis,*" *J. Biol. Chem.,* vol. 261, pp. 5341–5349 (1986); and Givannini et al., "Biosynthesis and degradation of peptides derived from *Xenopus laevis* prohormones," *Biochem. J.,* vol. 243, pp. 113–120 (1987). Zasloff showed that the Xenopus-derived peptides have antimicrobial activity, and renamed them magainins. Zasloff, "Magainins, a class of antimicrobial peptides from Xenopus skin: isolation, characterization of two active forms, and partial DNA sequence of a precursor," *Proc. Nati. Acad. Sci. USA,* vol. 84, pp. 3628–3632 (1987).

Synthesis of nonhomologous analogs of different classes of lytic peptides has been reported to reveal that a positively charged, amphipathic sequence containing at least 20 amino acids appeared to be a requirement for lytic activity in some classes of peptides. Shiba et al., "Structure-activity relationship of Lepidopteran, a self-defense peptide of Bombyx more," *Tetrahedron,* vol. 44, No. 3, pp. 787–803 (1988). Other work has shown that smaller peptides can also be lytic. See McLaughlin et al., cited below.

The synthetic lytic peptide known as S-1 (or Shiva 1) has been shown to destroy intracellular *Brucella abortus*-, *Trypanosoma cruzi*-, *Cryptosporidium parvum*-, and infectious bovine herpesvirus I (IBR)-infected host cells. See Jaynes et al., "In vitro effect of lytic peptides on normal and transformed mammalian cell lines," *Peptide Research,* vol. 2, No. 2, pp. 1–5 (1989); Wood et al., "Toxicity of a Novel Antimicrobial Agent to Cattle and Hamster cells In vitro," Proc. Ann. Amer. Soc. Anim. Sci., Utah State University, Logan, Utah. *J. Anim. Sci.* (*Suppl.* 1), vol. 65, p. 380 (1987); Arrowood et al., "Hemolytic properties of lytic peptides active against the sporozoites of *Cryptosporidium parvum,*" *J. Protozool.,* vol. 38, No. 6, pp. 161S–163S (1991); Arrowood et al., "In vitro activities of lytic peptides against the sporozoites of *Cryptosporidium parvum,*" *Antimicrob. Agents Chenother.,* vol. 35, pp. 224–227 (1991); and Reed et al., "Enhanced in vitro growth of murine fibroblast cells and preimplantation embryos cultured in medium supplemented with an amphipathic peptide," *Mol. Reprod. Devel.,* vol. 31, No. 2, pp. 106–113 (1992). Morvan et al., "In vitro activity of the antimicrobial peptide magainin 1 against *Bonamia ostreae,* the intrahemocytic parasite of the flat oyster *Ostrea edulis,*" *Mol. Mar. Biol.,* vol. 3, pp. 327–333 (1994) reports the in vitro use of a magainin to selectively reduce the viability of the parasite *Bonamia ostreae* at doses that did not affect cells of the flat oyster *Ostrea edulis.*

Also of interest are the designed peptides disclosed in McLaughlin et al., "Amphipathic Peptides," U.S. Pat. No. 5,789,542, issued Aug. 4, 1998; and Mark L. McLaughlin et al., "Short Amphipathic Peptides with Activity against Bacteria and Intracellular Pathogens," U.S. patent application Ser. No. 08/796,123, filed Feb. 6, 1997.

Lytic peptides such as are known generally in the art may be used in practicing the present inventions.

The complete disclosures of all references cited in this specification are hereby incorporated by reference. Also incorporated by reference are P. Schwarzenberger, "Development of a gene therapy based bone marrow purging system for leukemia patients," Abstract, 1998 Translational Research Progress Review Meeting, Leukemia Society of America (Sep. 24–25, 1998); P. Schwarzenberger, "Development of a gene therapy based bone marrow purging system for leukemia," slides presented at the Sep. 24–25, 1998 meeting of the Leukemia Society; and P. Schwarzenberger, "Development of a gene therapy based bone marrow purging system for leukemia patients," *Leukemia Society of America Annual Report* 1998, *Appendix: Abstracts of Grants in Force,* p. 82 (1999). In the event of an otherwise irreconcilable conflict, however, the present specification shall control.

We claim:

1. A method for purging leukemia cells from an in vitro or ex vivo cell mixture comprising leukemia cells and hematopoietic stem cells; said method comprising the steps of (a) transforming the cell mixture with an adenovirus-derived vector whose composition and concentration are such that the vector transforms substantially all leukemia cells in the mixture, and wherein the vector comprises a DNA sequence encoding a toxin, and a promoter that controls the expression of the DNA encoding sequence, wherein the promoter selectively causes transcription of the DNA sequence in a leukemia cell but not in a hematopoietic stem cell, and wherein the promoter is selected from the group consisting of the RSV promoter and the SV40 promoter; and (b) allowing the cell mixture to react for a time and under conditions sufficient to allow the toxin to kill those cells in which the toxin is expressed;

whereby:

substantially all of the leukemia cells are selectively killed, while a substantial number of the hematopoietic stem cells are not killed.

2. A method as recited in claim 1, wherein the promoter is the RSV promoter.

3. A method as recited in claim 1, wherein the promoter is the SV40 promoter.

4. A method as recited in claim 1, wherein the vector comprises a polylysine domain.

5. A method as recited in claim 1, wherein the vector is not adapted to cause the DNA encoding sequence and the promoter to incorporate into the genome of transformed cells, whereby the vector is not maintained in transformed cells indefinitely.

* * * * *